United States Patent [19]

Wen

[11] Patent Number: 4,644,335

[45] Date of Patent: Feb. 17, 1987

[54] APPARATUS AND METHOD FOR MONITORING DRILL BIT CONDITION AND DEPTH OF DRILLING

[75] Inventor: Sheree H. Wen, Mohegan Lake, N.Y.

[73] Assignee: International Business Machines Corp., Armonk, N.Y.

[21] Appl. No.: 720,340

[22] Filed: Apr. 5, 1985

[51] Int. Cl.[4] .......................................... G08B 21/00
[52] U.S. Cl. ................................. 340/683; 73/104; 73/660; 408/16; 340/680
[58] Field of Search .................. 340/683, 680; 408/6, 408/7, 15, 16; 73/104, 659, 587, 646, 660, DIG. 1

[56] References Cited

U.S. PATENT DOCUMENTS

| | | |
|---|---|---|
| 2,062,151 | 11/1936 | Weatherby . |
| 3,486,375 | 12/1969 | Redwine et al. . |
| 3,694,637 | 9/1972 | Edwin et al. ............ 408/6 |
| 3,841,149 | 10/1974 | Edwin et al. . |
| 4,007,631 | 2/1977 | Saifi et al. . |
| 4,087,801 | 5/1978 | Noh . |
| 4,150,568 | 4/1979 | Berger et al. . |
| 4,413,507 | 11/1983 | Drew et al. . |
| 4,478,538 | 10/1984 | Kakino ................. 340/683 |

Primary Examiner—Glen R. Swann, III
Attorney, Agent, or Firm—Scully, Scott, Murphy & Presser

[57] ABSTRACT

Acoustic transducers are attached to each of the drill bits which produce electrical output signals in response to the vibrations during the drilling operation. A plurality of output signal includes waveforms having an amplitude and frequency dependent upon the condition of the drill bit and the medium being drilled. The waveforms represent the acoustic signature produced by the drilling operation. A control unit simultaneously compares the acoustic signature of each of the output signals with a reference signal by comparing the waveforms to determine if an improper drill condition exits. When drilling through a multilayered workpiece such as a printed circuit board having layers of different types of materials, the acoustic transducers will produce an output signal having a sequence of waveforms representing the acoustic signatures of the sequence layers. The control unit counts the number of waveform occurrences for each particular type of layer and indicates when a predetermined level is reached. The control unit can also be programmed to stop the drilling operation upon reaching the desired layer.

12 Claims, 8 Drawing Figures

APPARATUS AND METHOD FOR MONITORING DRILL BIT CONDITION AND DEPTH OF DRILLING

DESCRIPTION

Technical Field

This invention relates to the automatic drilling machines and more particularly an apparatus and method for monitoring the condition of a drill bit and the depth of drilling in a workpiece.

BACKGROUND

In computer controlled automated mechanical drilling processes it is necessary to insure that the drill bit remains sharp and unbroken throughout the drilling operation. This is especially important in the drilling of printed circuit boards. In the manufacturing of single and multilayer circuit boards, holes are drilled through the board to accommodate the electrical connections required for the circuits. In many applications, the number of holes drilled can range from 4,000 to 10,000 holes. Generally, for drilling a large number of holes in the circuit boards, a drilling machine is used having multiple spindles. The large volume of holes being drilled requires that the drill bits be of a very small diameter. Currently, the drill bit being used is as small as 16 mil.

The use of these very fine drill bits causes the bits to become blunt or broken very easily during the drilling operation. Since the machines are automatically controlled, the drilling operation cannot be stopped and a broken or blunt drill will continue to spin and damage the boards. The holes drilled with a blunt or broken drill bit will be defective. This is not acceptable in the manufacture of circuit boards where accuracy is required. The defective holes must be reworked at a significant delay and expense. Frequently, proper reworking cannot be accomplished and an entire set of boards must be rejected.

Furthermore, in the manufacturing of multilayer circuit boards, it is often necessary to drill only to certain intermediate layers for the connections of the electrical circuits. However, heretofore there has not been available an efficient and accurate system for drilling multilayer boards to a predetermined depth. Thus, manufacturers are forced to drill through all the layers. In one approach to the problem, the machine is controlled by an operator to drill for a preselected time at a predetermined speed. This practice has been found to be unsuccessful because the drilling speeds vary as the drill bit progresses through inhomogeneous mediums. In addition, the operators must know precisely when the drilling commences and what the drilling speed is. Hence, the machine drills through more layers than is needed requiring additional electrical connections and unnecessary costs.

PRIOR ART

Prior art systems for monitoring drill bit condition include the detection of noise associated with the drilling operation. The noise is converted to an electrical signal that is analyzed to determine when the tool has become worn or broken.

One such system is disclosed in U.S. Pat. No. 4,413,507 issued to Drew et al. wherein noise emission signals associated with the cutting operation of the tool are compared to a standard signal to determine when the tool has become worn. If the level of noise detected exceeds a threshold level an output signal indicates that the cutting tool has become blunt. The Drew et al. apparatus would not be useful in the drilling of multilayer circuit boards where different layers produce signals of varying amplitude. Furthermore, the Drew et al apparatus does not address the problem of the detection of drill bit condition on a multiple spindle drilling machine.

U.S. Pat. No. 3,486,375 issued to Redwine et al. discloses and apparatus for determining the lithologic condition of underground rock formations. A transducer is provided on the drilling apparatus that transmits electrical signals to the surface in accordance with the acoustic vibrations produced by the drilling machine. The signals are recorded on a strip chart recorder where the different amplitude levels of the output signal can be observed to determine which type of rock formation is being drilled. The Redwine et al. apparatus is not suitable for determining the depth of drilling in a multilayered workpiece having a known sequence of layers. In addition, the Redwine et al. device does not address the problem of determining the depth of a plurality of drill bits on a multiple spindle drilling machine.

SUMMARY OF THE INVENTION

The present invention provides an apparatus and method for monitoring the depth of a drilling operation and the condition of the drill bit. In the drilling of single layer or multilayer circuit boards, where single or multiple spindle drilling machines are used, a detector is provided to monitor the condition of the drill bits in the drill machine. The detector includes a plurality of acoustic detecting transducers attached to the machine for producing an electrical output signal in response to the vibrations of each of the drill bits. The vibrations will have a particular acoustic signature depending on the condition of the drill bit and the medium being drilled. The output signal is an electrical representation of the particular acoustic signature produced during drilling. The acoustic signature is represented by a waveform having a particular amplitude and frequency. A control unit simultaneously compares each of the output signals with a reference signal stored in the control unit. The reference signal represents the acoustic signature obtained by a normal drill bit. The acoustic signatures during the drilling of a workpiece are compared to detect changes in the acoustic signature from the reference signature. An improper drill condition exists when an output signal has an amplitude lower than the amplitude of the reference signal. In addition, a change in the frequency of the output signal from the reference frequency will also indicate an improper drill condition. A display having individual indicating lights is provided to indicate to the operator of the machine that a particular drill bit is blunt or broken. A computer may be included to automatically stop the drilling of the particular spindle that has the blunt or broken drill bit so that the bit can be replaced before damaging the circuit board.

In another embodiment of the present invention, the apparatus can be utilized to monitor the depth that the drill bit has drilled into to a multilayered workpiece in order to be able to drill to any desired layer. An acoustic transducer is connected to the top layer of the circuit board and produces a sequence of output signals in response to the vibration caused by drilling through each of the layers. Each particular type of layer produces an output signal representing a different acoustic signature.

A control unit has stored within its memory reference signals equal to the known acoustic signatures for each type of layer. The control unit compares the acoustic signature of the output signals to the reference signal and counts the number of occurrences of each acoustic signature for each type of layer. The control unit can be programmed to stop the drilling operation upon reaching a predetermined number of acoustic signatures for any particular layer. Thus, the apparatus can be used to drill to any predetermined level in order to make the proper interconnections for the electrical circuits.

Hence, the present invention results in very accurate drilling utilizing very fine drill bits, such as within a 10 to 12 mil diameter. In addition, the smaller drill bits allow for more connections to the electrical circuits thereby increasing the circuit density of the boards. Only the layers to be interconnected are drilled by the apparatus thereby eliminating the problem of needlessly drilling through all the layers of the circuit board.

Furthermore, a computer can be provided for storing a particular sequence of signals in accordance with the known multilayer configuration. The computer can compare the actual sequence of output signals with the reference sequence to determine if all the proper layers are provided within the circuit board. Thus, previous process steps of manufacturing the circuit boards can be monitored.

DETAILED DESCRIPTION OF THE PREFERRED EMBODIMENT OF THE INVENTION

Figure 1:
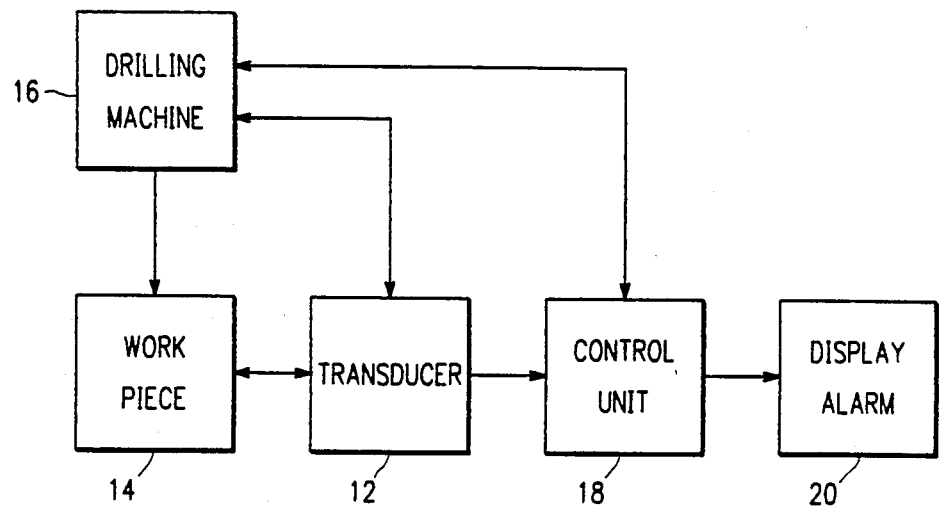
FIG. 1 is a block diagram of the apparatus of the present invention.
Figure 3:
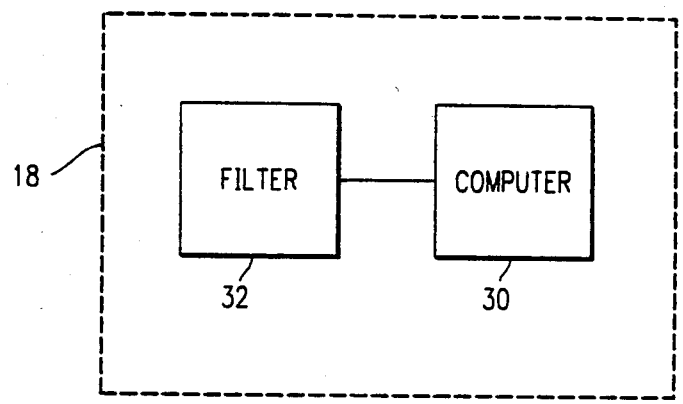
FIG. 3 is a block diagram of the control unit for the apparatus of the present invention.

Referring now to the drawings, FIG. 1 shows a block diagram of an illustrative embodiment of the apparatus of the present invention. The apparatus consists of a transducer 12 for producing electrical output signals in response to the vibrations caused by the drilling operation. The transducer 12 may be either connected to the workpiece 14 or to any part of the drilling machine 16 such as the spindle. The transducer 12 converts the vibrations into electrical signals and the output of the transducer is fed to a control unit 18. The control unit 18 is designed to perform the various functions of the apparatus. The control unit can be programmed to compare the output signal from the transducer 12 with a reference signal to produce a signal activating a display/alarm 20 when an improper drill condition is detected. The control unit 18, as shown in FIG. 3, may include a computer 30 and a feedback connection to the drilling machine 16 to automatically stop the machine when an improper drill condition is detected.

The electrical output signal from the transducer 12 will be a waveform of a particular amplitude and frequency dependent on the condition of the drill bit. This waveform represents the acoustic signature of the drill bit. The reference signal has an established acoustic signature determined from normal drilling with a drill bit in proper condition. The acoustic signatures of the output signal and the reference signal are continuously compared by the control unit 18. During normal drill bit conditions, the output signature will be equal to the reference signature. When a drill bit becomes blunt or broken, the output acoustic signature will vary from the reference signature. The blunt or broken drill bit will produce, at the transducer 12, a waveform having an amplitude or frequency different than the reference signal. Generally, the output signal will have an amplitude lower than the established reference signal. This difference is then detected by the control unit 18 and an alarm or display is activated. In computer controlled operations, the drilling machine will be automatically stopped to permit the drill bit to be replaced. Thus, the reworking of circuit boards or the rejection of entire boards is greatly reduced by the present invention.

Figure 2:
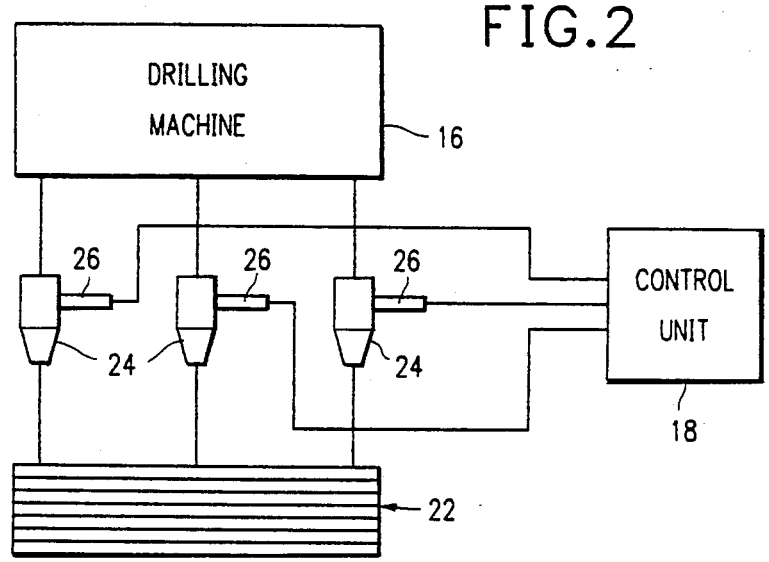
FIG. 2 is a sketch of a multiple spindle drilling machine for drilling a multilayer circuit board.

The apparatus of the present invention is especially well suited for use in the drilling of printed circuit boards. In this embodiment, multilayer boards are drilled by a drilling machine having a plurality of spindles and drill bits for drilling a multiplicity of holes simultaneously. FIG. 2 is a sketch showing a multilayer circuit board 22 being drilled by drilling machine 16 having a plurality of spindles and drill bits 24. An acoustic transducer 26 is connected to each of the spindles 24 for simultaneously converting vibrations from each spindle to electrical output signals and transmitting those signals to the control unit 18. In this embodiment, it is preferred that a separate transducer be connected to each spindle or drill bit. However, the apparatus may function with one transducer connected to the circuit board if the control unit is designed to discriminate between the intensity of the signals depending upon the distance the drill bits are from the transducer.

The transducer detector 26 may be any type of acoustic detection device such as a piezoelectric crystal, microphone, or phonograph cartridge. Furthermore, the acoustic contact between the transducer and the spindle may be gas, grease, mechanical coupling, liquid or an acoustic rod which can transfer the acoustic signals from the board, spindle, or drilling machine to the detector device.

In the embodiment shown in FIG. 2, the control unit 18 will simultaneously compare each of the output signals from each spindle with the reference signal. If the acoustic signature of one or more of the drill bits varies from the reference signature, the control unit 18 will stop the drilling machine and actuate the display/alarm 20. In computer controlled operations, the computer can be programmed to stop only the spindle or spindles having the blunt or broken drill bit, while the other spindles continue to drill, thereby saving valuable work time. Parallel signal processing may be used in order to discriminate between the acoustic signatures of the multiple spindles and only stop that spindle having the blunt or broken drill.

Figure 6:
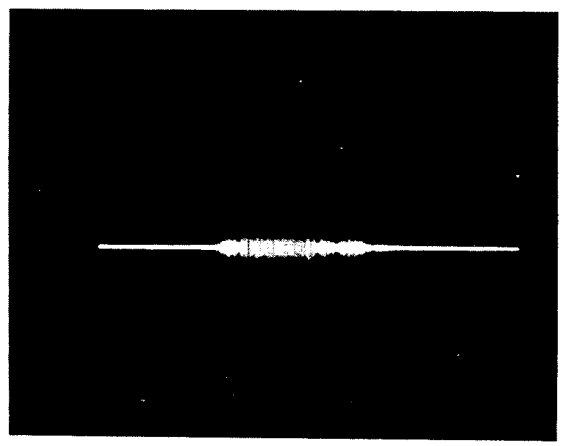
FIG. 6 is a photograph of an oscilloscope trace of an output signal as seen with a broken drill bit.
Figure 5:
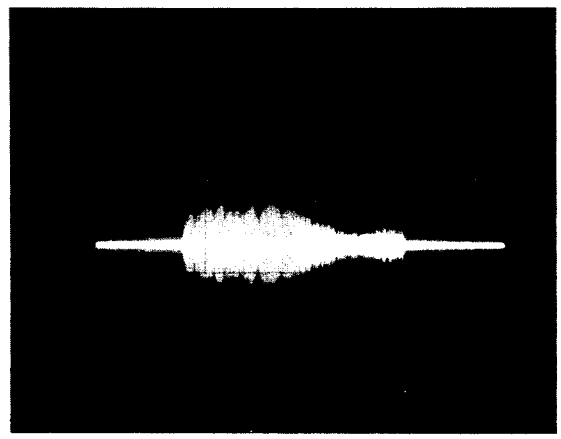
FIG. 5 is a photograph of an oscilloscope trace of an output signal as seen during normal drilling.
Figure 4:
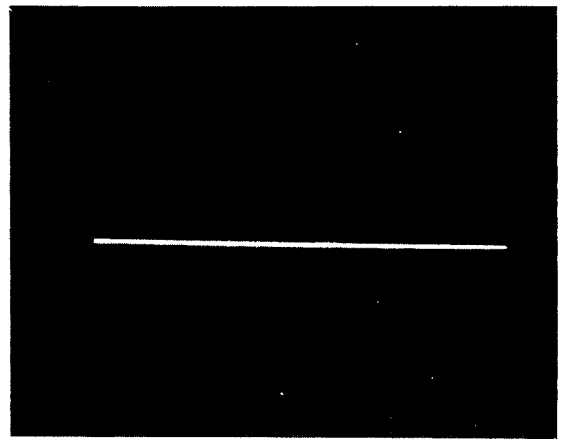
FIG. 4 is a photograph of an oscilloscope trace of the output signal as seen before the drilling operation.

FIGS. 4, 5 and 6 are photographs of oscilloscope traces obtained from the operation of the apparatus of the present invention. A 300 khz piezoelectric transducer was used and a quartz rod was employed to establish acoustic contact between the transducer and the circuit board. FIG. 4 shows the oscilloscope trace with a broken drill bit or before drilling. FIG. 5 shows the trace obtained during the drilling process employing an undamaged drill. FIG. 6 shows the oscilloscope trace when the drill had a 2 mil chip from the tip. As can be seen from comparing FIGS. 5 and 6, the damaged drill bit shows an evident decrease in acoustic amplitude.

To facilitate the detection of this decrease, the control unit 18, as shown in FIG. 3, may include a filter means 32 for filtering out noise from the environment such as human talking, floor vibration, or movement of the machine itself. A band pass filter is generally used since the above-mentioned noise will generally be in a low frequency range. In addition, there are also high frequency noises that should be filtered out. The filter can be designed to permit the detection of only a particular window or range of frequencies to filter out both low and high frequency noises.

The drill bit condition detector of the present invention minimizes and may largely eliminate the need for visual inspection of the drill bit during the drilling process. It eliminates the need for reworking holes that were improperly drilled between a drill failure and a detection of the broken drill by periodic inspection. Costs and wastage due to the reworking of boards drilled with defective bits will be greatly reduced.

In computer controlled operations, the apparatus will permit real time monitoring of the interval between drill failures. It is then possible to measure and maintain acoustic statistics on drill bit lifetime. A defective batch of drill bits can then be detected at an early stage due to the difference in life time statistics from the established norm.

In addition to detecting blunt or broken drill bits, abnormal acoustic signatures may also indicate drill misalignment or misregistration, incorrect drilling speed or incorrect rotating speed. The control unit 18 and the display 20 can be modified accordingly to warn the operator of these different abnormal conditions.

Figure 7:
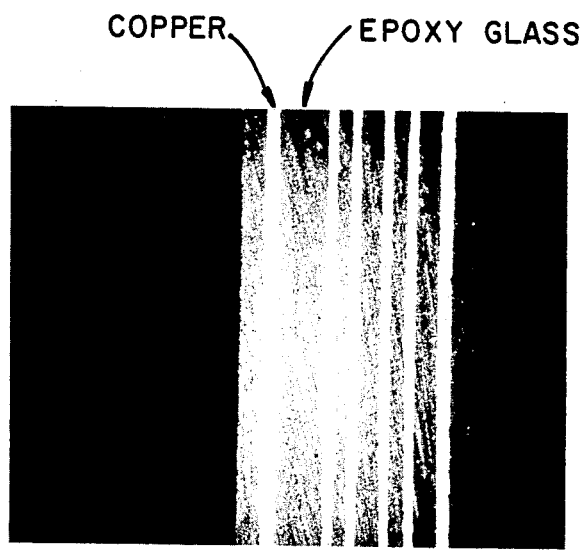
FIG. 7 is a photograph of a cross-section of a multilayer circuit board.

In another embodiment of the present invention, the apparatus can be used to monitor the depth of drilling through the workpiece. This is especially useful in drilling the multilayer circuit boards. FIG. 7 is a cross section of a typical multilayer circuit board having alternating layers of epoxy-glass and copper. In this embodiment, transducer 12 will be attached to the top layer of the circuit board 22. The transducer 12 produces an electrical output signal in response to the vibrations caused by drilling through each layer of the circuit board 22. The acoustic signature, as represented by the electrical output signal, will depend upon the particular medium being drilled. As stated above, the acoustic signature will be reflected by a waveform of a particular amplitude and frequency. The output signal will therefore include a sequence of waveforms, where each of the waveforms represent the acoustic signature of the medium being drilled. For the two-medium circuit board shown in FIG. 7, there will be two distinct acoustic signatures reflected in two waveforms each having different amplitudes and frequencies. Thus, it can easily be determined which particular layer the drill bit is drilling through by a count of the number of occurrences of the waveforms representing the acoustic signature for each type of medium.

The control means 18 compares the waveforms of the output signal to a reference signal for each type of layer and counts the number of occurrences of the waveform for each layer. The count may be of the number of occurrences of the particular amplitude level or of particular frequency for each layer. The control unit 18 can then automatically stop the machine upon reaching the predetermined count of waveform occurrences for a particular layer type.

Figure 8:
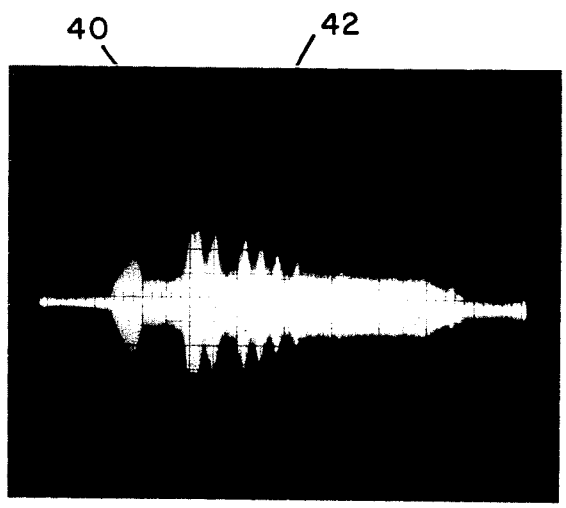
FIG. 8 is a photograph of an oscilloscope trace showing the output signal of the transducer when drilling through the circuit board of FIG. 7.

FIG. 8 shows the the oscilloscope trace when using a 16 mil drill bit to drill through the circuit board shown in FIG. 7. The acoustic signal was detected by a piezoelectric transducer at 300 khz which was attached to the circuit board on its upper face, the face which is in contact with the drill. The acoustic emission pattern shows a high amplitude emission 40 during the period in which the drill bit is passing through the epoxy-glass layers and a low amplitude emission 42 during the period in which the drill is passing the copper layers.

In operation, if it is desired to drill to the top of a particular intermediate layer, such as copper, in a multilayer circuit, the layer number is entered into the computer control 18. The computer control unit 18 is thereby externally programmed to detect the arrival of the drill at this particular layer by counting the number of amplitude levels representative of copper layers. Upon detecting the change in the acoustic pattern for the desired layer number, the computer can then instruct the drill to cease operation from that point in time. If, alternatively, it is desired to drill through a particular copper layer, the output change in amplitude can be used to detect the penetration of the copper and the computer can likewise instruct the drill to cease operation at that point. Similarly, changes in the frequency of the output signal can be counted by the computer to control the drilling depth. It is therefore possible to employ acoustic signal emission to accomplish drilling through any predetermined point within a multilayer circuit board.

The present invention makes it possible to drill holes into a multilayer circuit board to any predetermined point within the board in a more accurate and controlled way. The present invention creates the possibility of layering the circuits which can be accessed for connection to a particular chip for proper interconnection of the circuits. Thus, there is no longer a need to drill through all the layers of a circuit board, thereby eliminating unnecessary connections and decreasing costs. The present invention permits the interconnection of only the layers that are required to be connected. The combination of the blunt or broken drill bit condition detector and the drill bit depth detector into one bit detection apparatus would enable the use of very fine drills, within the 10 to 12 mil diameter range. The use of these smaller drills would allow the interconnection of more circuits thereby increasing the circuit density of the circuit boards.

Furthermore, in carrying out the drilling operation in a constant and predetermined way, the change in amplitude as the drill bit progresses through the various layers in a multilayered circuit will yield the spacial sequence of the layers within the board. By comparing the detected spacial sequence from the actual operation with a theoretical sequence developed on the basis of the internal geometry of the multilayer circuit, it is possible to determine in real time whether there is any misregistration between the work piece and the drill bits. This misregistration might consist of improper orientation or alignment of the workpiece or an improper alignment of the drill bit. In addition, the proper geometry of the board can be tested by matching the sequence with the reference sequence. Thus, previous steps in the manufacturing of the circuit board can be tested. The computer can be modified to provide signals on the display indicating the type of problem detected.

While the invention has been particularly shown and described with respect to preferred embodiments thereof, it will be understood by those skilled in the art that the foregoing and other changes in form and details may be made therein without departing from the spirit and scope of the invention.

Having thus described our invention, what I claim as new and desire to secure by Letters Patent is:

1. A apparatus for drilling to a predetermined depth of a multilayered workpiece, the drilling of said workpiece causing vibrations having a particular acoustic signature dependent upon the medium being drilled, said apparatus comprising;
   an acoustic detector means for producing an output signal in response to the vibrations caused by drilling through the layers of said workpiece, said output signal having a sequence of waveforms representing the acoustic signatures of the layers;
   control means for comparing the output signal to a reference signal for each type of layer, and for counting the number of occurrences of the waveform representing the acoustic signature for each type of layer; and
   means for stopping the drilling operation upon reaching a predetermined count of waveform occurrences for a particular layer type.

2. The apparatus of claim 1 wherein said control means includes a computer for comparing the detected sequence of waveforms to a reference sequence of waveforms stored in said computer corresponding to the multilayered configuration of said workpiece.

3. The apparatus of claim 2 further including a means for indicating when the detected sequence of waveforms differs from, said reference sequence.

4. The apparatus of claim 1 wherein said acoustic detecting means is a piezoelectric transducer.

5. The apparatus of claim 1 wherein said acoustic detecting means is attached to the upper surface of said multilayered workpiece.

6. In a multiple bit drilling machine, an apparatus for controlling the drilling depth of each drill bit into a multilayered workpiece, each of said drill bits causing vibrations having a particular acoustic signature dependent upon the medium being drilled, said apparatus comprising:
   a plurality of acoustic detecting means for producing a plurality of output signals in response to the vibrations caused by each drill bit as the bit drills through each layer of said workpiece, each of said output signals having a sequence of waveforms representing the acoustic signatures of the layers;
   control means for comparing each of said output signals to a reference signal for each type of layer, and for counting the number of occurrences of the waveform representing the acoustic signatures for each type of layer for each signal; and
   means for separately stopping the drilling operation of at least one drill bit upon reaching a predetermined count of waveform occurrences for a particular layer type for each drill bit.

7. The apparatus of claim 1 or 6 further including a filter means for filtering out low and high frequency noise.

8. In a multiple bit drilling machine, an apparatus for monitoring the condition of a plurality of drill bits and for monitoring the drilling depth in a multilayered workpiece, each of the drill bits causing vibrations having a particular acoustic signature dependent on the condition of the drill bit and the medium being drilled, said apparatus comprising:
   a plurality of acoustic detecting means for producing a plurality of output signals in response to the vibrations of each of said plurality of drill bits, each of said output signals having a sequence of waveforms representing the acoustic signatures of the layers;
   control means for simultaneously comparing each of said output signals to a reference signal, said reference signal representing an acoustic signature for a proper drill bit drilling having each type of layer, for counting the number of occurrences of the waveform representing the acoustic signature for each layer type for each of said drill bits, and for detecting when the acoustic signature of at least one of said output signals is different from the acoustic signature of said reference signal thereby detecting an improper drill bit condition; and
   means for stopping the drilling operation of at least one drill bit upon detection of an improper drill bit condition; and
   means for stopping the drilling operation of at least one drill bit upon reaching a predetermined count of waveforms occurrences of a particular layer type for one or more drill bits.

9. A method for drilling to a predetermined depth of a multilayer workpiece comprising:
   acoustically detecting drill bit vibrations as the drill bit passes through each layer of the workpiece, the vibrations having a particular acoustic signature dependent upon the medium being drilled;
   producing an electrical output signal in response to said vibrations, said output signal having a plurality of waveforms representing the acoustic signatures of the layers;
   comparing the output signal to a reference signal for each type of layer;
   counting the number of occurrences of the waveform representing the acoustic signatures for each type of layer; and
   stopping the drilling operation upon reaching a predetermined count of waveform occurrences for a particular layer type.

10. The method of claim 9 further including the steps of producing an output signal having a sequence of waveforms representing the acoustic signatures corresponding to the sequence of layers, comparing the sequence of waveforms to a reference sequence and stopping the drilling operation upon detecting a difference between the output sequence and the reference sequence.

11. The method of claims 9 or 10 wherein said drilling operation includes a multiple drill bit machine wherein a plurality output signals are produced and simultaneously compared to said reference signals.

12. In a multiple bit drilling operation, a method for monitoring the condition of a plurality of drill bits and for monitoring the drilling depth in a multilayered workpiece; said method comprising;

acoustically detecting the vibrations of each said drill bit as the drill bit passes through each layer of the workpiece, the vibrations having a particular acoustic signature dependent upon the medium being drilled and the condition of the drill bit;

producing an electrical output signal for each drill bit in response to said vibrations, each of said output signals having a sequence of waveforms representing the acoustic signatures corresponding to the sequence of layers of the workpiece;

simultaneously comparing the output signal for each type of layer with a reference signal for each type of layer;

counting the number of occurrences of the waveform representing the acoustic signature for each type of layer;

detecting when the acoustic signature of said output signal is different from the acoustic signature of said reference signal;

stopping the drilling operation of at least one drill bit upon the detection of a difference between the acoustic signature of at least one of said output signals and said reference signal; and stopping the drilling operation of at least one drill bit upon reaching a predetermined count of waveform occurrences for a particular layer type for one or more drill bits.

* * * * *